United States Patent
Meschonat et al.

(10) Patent No.: US 6,221,406 B1
(45) Date of Patent: Apr. 24, 2001

(54) ENZYME PRE-GRANULES FOR GRANULAR FODDER

(76) Inventors: Beate Meschonat; Hubert A. Herrmann; Rolf Spannagel; Vera Sander; Gerhard Konieczny-Janda; Mario Sommer, all of Hoechst Marion Roussel Deutschland GmbH Patent- und Lizenzabteilung, Geb. K 801, D-65926 Frankfurt am Main (DE)

( * ) Notice: Subject to any disclaimer, the term of this patent is extended or adjusted under 35 U.S.C. 154(b) by 0 days.

(21) Appl. No.: 09/180,617

(22) PCT Filed: May 6, 1997

(86) PCT No.: PCT/EP97/02306

§ 371 Date: Feb. 25, 1999

§ 102(e) Date: Feb. 25, 1999

(87) PCT Pub. No.: WO97/42837

PCT Pub. Date: Nov. 20, 1997

(30) Foreign Application Priority Data

May 13, 1996 (DE) ................................................ 196 19 219

(51) Int. Cl.[7] ................................ A23C 9/12; A23B 4/03
(52) U.S. Cl. ............................ 426/63; 426/453; 426/454; 426/461; 426/463
(58) Field of Search .................................... 426/461, 453, 426/454, 463, 63

(56) References Cited

U.S. PATENT DOCUMENTS

| 3,764,708 | * | 10/1973 | Aonuma et al. | 426/46 |
| 3,869,558 | * | 3/1975 | Hampton et al. | 426/443 |
| 4,903,414 | * | 2/1990 | White et al. | 34/15 |
| 5,391,371 | * | 2/1995 | Jacobsen et al. | 424/94.2 |

FOREIGN PATENT DOCUMENTS

| 257996 | * | 3/1988 | (EP) . |
| 62-269685 | | 11/1987 | (JP) . |
| WO 9211347 | | 7/1992 | (WO) . |
| WO 9212645 | | 8/1992 | (WO) . |
| WO 9518544 | | 7/1995 | (WO) . |
| WO 9716076 | | 5/1997 | (WO) . |
| 97/42839 | * | 11/1997 | (WO) . |
| 97/43482 | * | 11/1997 | (WO) . |

* cited by examiner

Primary Examiner—Jon P. Weber
(74) Attorney, Agent, or Firm—William M. Blackstone

(57) ABSTRACT

The invention relates to the preparation of enzyme pregranules with stable activity which can be incorporated into particles of a granular animal feed. The invention further relates to the pregranules with stable activity which are obtained by the preparative processes and can be incorporated into granular animal feeds.

25 Claims, No Drawings

ENZYME PRE-GRANULES FOR GRANULAR FODDER

This application is the 35 USC 371 national phase application of PCT/EP97/02306, filed May 6, 1997, which claims priority to German application 196 19 219.6, filed May 13, 1996.

The invention relates to the preparation of enzyme pregranules with stable activity which can be incorporated into particles of a granular animal feed. The invention further relates to the pregranules with stable activity which are obtained by the preparative processes and can be incorporated into granular animal feeds.

The use of enzymes in animal feeds makes it possible to improve the utilization of the nutrients contained in the animal feed, since the addition of enzymes facilitates the utilization of constituents which the animal cannot completely or easily digest. The addition of enzymes to animal feed proves to be an effective means of developing feeds in an unconventional and value-for-money preparation which guarantees optimum utilization of the nutrients contained in the feed. This makes it possible to use value-for-money raw materials, such as cereals, beans or other seeds, in an optimum manner for the manufacture of high-quality feed components which are also particularly suitable for young animals. An extensive number of enzymes with special activities for the degradation of special feed constituents, e.g. glucans, starch, proteins, pectin-like polysaccharides, phytic acid, galactomannans, galactoarabans, polygalacturones, raffinose, stachyose, hemicellulose, cellulose, pentosans and other nutrient constituents, are available for use in animal feeds. Animal feeds frequently take the form of granules, i.e. comparatively coarse or granular aggregates; those skilled in the art of animal feeds then often speak of "pelleted feeds", even though the shape of the granular particles is not rounded in the true sense of the word "pellet" (spherical particle). The enzymes can be admixed to the feed, a feed premix or a mixing constituent, or can be incorporated into granules of these constituents. Granular enzyme products can very easily be mixed with the feed components provided that these enzyme granules are based on ordinary feed components, e.g. wheat or soya flakes. In the state of the art, processes are also known in which dissolved enzymes are sprayed onto particles of feed in a fluidized, moving or agitated bed and then dried if appropriate. The disadvantage here is that an undesirable bacterial contamination of the feed is often observed. It may further be desirable to incorporate the enzymes directly into the particles of a granular animal feed in order to maximize the intimacy and homogeneity of mixing of the enzyme in the particles of the granular animal feed itself. In the manufacture of such a granular feed, the desired constituents of the animal feed are therefore mixed with an enzyme preparation and the mixture is subsequently conditioned with a jet of steam and then extruded into pellets. In the manufacture of such granular animal feeds, however, the added enzymes are subjected to high temperature and pressure stresses and friction and shear forces. This often not only greatly impairs the original enzymatic activity but can even destroy it altogether.

The object was therefore to provide a suitable procedure for the formulation of enzymes for feeds in order to overcome the above disadvantages and make it possible to incorporate the enzymes into the particles of a granular animal feed homogeneously and without substantial losses of activity.

The object is achieved by the process indicated in claim 1, by the enzyme pregranules with stable activity according to claim 16, prepared by these processes, and by the use indicated in claim 18. Advantageous embodiments of the process according to the invention are described in subsidiary claims 2 to 15 and, in respect of the enzyme pregranules according to the invention, in subsidiary claim 17.

Accordingly, the invention provides a process for the preparation of enzyme pregranules with stable activity which can be incorporated into the particles of a granular animal feed, a feature of the process according to the invention being that moist granules are first prepared by a procedure in which 0.01 to 20 parts by weight of enzyme or enzyme mixture (calculated as the solids content of the enzyme preparation used), 80 to 99.99 parts by weight (including moisture content) of an organic flour grade with an extraction rate of 30% to 100%, the flour grade having been obtained by grinding a flour base which may have been washed and/or purified beforehand and has been treated with dry superheated steam, and the parts by weight of the enzyme or enzyme mixture and the flour grade totaling 100, and, if desired, up to a total of 20 parts by weight of granulation aids (calculated as anhydrous granulation aids), are converted to adhesive-free moist granules with the desired particle size range by intimate mixing in a high-speed mixer, using a calculated amount of water which is sufficient to adjust the moisture content of the moist granules to 20 to 50% by weight (based on the sum of the constituents of the moist granules as 100% by weight), and the moist granules obtained in this way are dried and then, if desired, freed of undersize and/or oversize material by screening. The term "adhesive-free" means here that the moist granules no longer adhere to the mixing elements or the mixer wall.

In an advantageous embodiment of the invention, a feature of the above process is that the moist granules are prepared using 0.01 to 10 parts by weight of enzyme or enzyme mixture, preferably 2 to 7 parts by weight of enzyme or enzyme mixture, 90 to 99.99 parts by weight of flour grade, preferably 93 to 98 parts by weight of flour grade, if desired, up to a total of 15 parts by weight, preferably 0.5 to 5 parts by weight, of granulation aids, and a calculated amount of water which is sufficient to adjust the moisture content of the moist granules to 25 to 40% by weight, preferably 25 to 35% by weight.

According to the invention, organic flours (i.e. flours from organic basic substances) of a particular type are used. Within the framework of the invention, the term "organic flour" includes any more or less comminuted, pulverulent to finely granular products which have been obtained by comminution (grinding) from solid organic materials of natural origin (flour base). Advantageously, the process according to the invention uses organic flours which are obtained by grinding grain, leguminous fruits and/or fruits of the Malvaceae family (e.g. cottonseed). The cereals preferably used as the flour base within the framework of the invention are especially wheat or rye, but barley, oats, rice and maize, as well as sorghum and other varieties of millet, can also be used. Although buckwheat per se does not belong to the cereal varieties (knotgrass plant), its beechnut-like farinaceous fruits can also be used as a flour base within the framework of the invention; this applies particularly to granular poultry feeds, but caution may be advisable in the manufacture of granular fodder for grazing cattle because of the content of photosensitizing fagopyrine, if it is intended to feed it to predominantly white-haired cattle. In another preferred variant of the invention, leguminous fruits are used as the flour base. Legumes are understood here as meaning the vegetable foods (pulses) belonging to the fruiting vegetables. Possible flour bases within the framework of the invention are therefore the fruits of the leguminous varieties, such as: Pisum (garden pea), Cajamus (cajan pea), Cicer (chick pea); Lens (lentil); Phaseolus (kidney bean), Vigna (cow bean), Dolchius (hyacinth bean), Cassavalia (sword bean), Vicia (horse bean or vetch); field pea; Arachis (groundnut); lupin; alfalfa; soya bean, Lima bean and, where appropriate, other pulses as well as Malvaceae fruits (e.g. of the genus Gossipium, cotton). Soya beans are preferred.

Among oil-containing fruits of the above varieties, it is possible to employ deoiled, partially deoiled and oil-containing fruits to obtain the flour used according to the invention; partially deoiled fruits, especially partially deoiled leguminous fruits, e.g. partially deoiled soya beans, are preferred for this purpose.

Depending on the grinding processes applied and the extraction rate thereby achieved, the flours which can be used within the framework of the invention are fine powders with a yellowish white to gray/dark color (light or dark flours) or, if appropriate, more or less granular products (coarse meal, farine, fine farine) or products streaked with white/yellowish brown. The organic flour grades used according to the invention normally have a moisture content of up to about 15% by weight (e.g. a moisture content of 7 to 15% by weight), which is to be taken into account when calculating the percentage moisture content of the moist granules prepared according to the invention in the high-speed mixer. The cereal flours conventionally used in the invention are those with a moisture content of about 10 to 15% by weight, especially 13 to 15% by weight; the flours of leguminous fruits or fruits of the Malvaceae family conventionally have a moisture content of about 9(±2)% by weight.

Other important criteria for the characterization of the flour type used according to the invention are the extraction rate and the so-called flour grade; these criteria correlate with one another such that the identification number of the flour grade (i.e. of the degree of comminution or the fineness of the flour) increases with increasing extraction rate. The extraction rate corresponds to the amount by weight of flour obtained, based on 100 parts by weight of grinding stock used (i.e., within the framework of the invention, 100 parts by weight of the cereal or leguminous fruits used); it is thus a percentage flour yield. Grinding of the flour initially gives mainly pure, very fine flour, e.g. from the inside of the grain; as grinding continues, i.e. with increasing extraction rate, for example, the crude fiber and husk content of the flour increases, the proportion of starch-thereby decreasing. The extraction rate is therefore also reflected in the so-called "flour grade", which is used as a figure for classifying flours—especially cereal flours—and is based on the ash content of the flour (so-called ash scale). The flour grade or type number indicates the amount of ash (minerals) in mg which is left behind when 100 g of flour solids are incinerated. Taking cereal flours as an example, the type number can be explained as follows: the higher the type number, the darker the flour and the higher the extraction rate, because the nucleus of the grain contains only about 0.4% by weight of ash, but the husk contains around 5% by weight. Thus a grade 405 wheat flour contains e.g. an average of 0.405% by weight of ash. In the case of a low extraction rate, on the other hand, the cereal flours consist predominantly of the comminuted endosperm, i.e. the starch constituent of the grains; when the extraction rate is higher, the cereal flours also contain the comminuted, protein-containing aleurone layer of the grains; in the case of coarse meal, they also contain the constituents of the protein-containing and fat-containing embryo and of the seed husks containing raw fiber and ash.

The extraction rate of the flour used according to the invention is 30% to 100%. An extraction rate of 30% corresponds to a very fine flour and an extraction rate of 100% to a wholemeal flour. In advantageous variants of the process according to the invention, a feature of said process is that the extraction rate of the flour grade is 50% to 100%, preferably 70% to 100%.

A feature of the flour used in the process according to the invention is that it has been obtained from a flour base which, before grinding, has been subjected to a treatment with dry superheated steam at a temperature of particularly 100 to about 110° C., under approximately normal pressure to a slight excess pressure (e.g. 0.8 to 1.2 bar of excess pressure), for a treatment time (residence time in the superheated steam treatment device described below) of up to about 1 hour. Dry superheated steam is a superheated unsaturated steam which can be produced in conventional manner by superheating and separation of any water condensate or by expansion of high-pressure steam. The superheated steam treatment of the flour base can be carried out e.g. using a conical bunker widening at the bottom, which is equipped with one or more annular nozzles or steam lances for introducing the dry superheated steam. The bunker can be charged continuously with the flour base, e.g. via screw conveyors, and discharged via heated screw conveyors. The flour base treated with superheated steam is then conditioned to a constant water content of at most 15% by weight, e.g. in a downstream fluidized bed dryer, and cooled in another fluidized bed dryer for subsequent grinding. The treated and cooled flour base is then fed continuously into a grinding machine and ground thoroughly to a particle size distribution with the bulk of the particle sizes in the range 500 to 50 $\mu$m; preferably, the proportion of particles with sizes below 50 $\mu$m in the ground flour does not exceed 35% by weight and the proportion of particles with sizes of 300 to 500 $\mu$m in the ground flour does not exceed 10% by weight. In an advantageous particle size distribution, the proportion of particles >300 µm is at most 5% by weight, the proportion of particles in the range 300 µm to 50 µm is 65 to 80% by weight and the proportion of particles below 50 µm is at most 30% by weight.

In the process according to the invention, the mixing and granulation of the constituents can take place in a batch high-speed mixer, e.g. of the ploughshare mixer type, or in a continuous high-speed mixer, for example of the Schugi Flexomix type (manufactured by Schugi Process Engineers in Lelystadt/NL). Adhesive-free moist granules are obtained here by a procedure in which water is continuously metered in, if appropriate by way of an enzyme solution or with any added granulation aid, as a function of the introduction of the main solid constituents, in such a way that the moisture content of the moist granules (i.e. before drying) at the mixer outlet is generally 20 to 50% by weight, preferably 25 to 40% by weight and especially 25 to 35% by weight. The moist granules produced by the process according to the invention have a particle size range of 50 to 800 µm, preferably 100 to 800 µm and especially 100 to 500 µm. In the process according to the invention, the mixing time in the high-speed mixer, or the average residence time in the case of continuous operation, is normally up to a maximum of 15 minutes; those skilled in the art can adapt the mixing time or residence time to the desired properties of the moist granules (e.g. freedom from adhesion, particle sizes) or to the particular mixer. Periods of about 2 minutes to 10 minutes, especially 3 to 8 minutes, have proved adequate as advantageous mixing or residence times in the case of batch granulation. For continuous operation, appreciably shorter average residence times in the mixer are also adequate; thus, in the case of continuous operation in a high-speed mixer of the Schugi Flexomix type, an average residence time in the region of only a few seconds, e.g. up to 30 seconds, especially 1 to 10 seconds, depending on the size of the apparatus and the flow rate, is sufficient. Following granulation, the moist granules are subjected to conventional drying under conditions which are mild for the enzymes, e.g. in a fluidized bed dryer, and dried to give granules with a desired moisture content, especially a moisture content of 3 to 12% by weight, preferably 7 to 9% by weight. After drying, the enzyme pregranules can now be covered with a lacquer or a coating in a manner which is conventional per se. The coating or lacquer can contain another enzyme or can be used to color the granules, or else they can delay the release of the enzyme or enzyme mixture, e.g. including pH-dependent release in different gastrointestinal regions. The lacquer or coating here can be applied either continuously or batchwise to the enzyme pregranules.

In the process according to the invention, it is possible per se to use any enzymes which have a favorable effect on the utilization or digestibility of nutrient constituents in animal feeds. The enzyme here can be an isolated pure enzyme (i.e. without secondary activities) or a mixture of enzymes. An enzyme mixture can be made up of pure enzymes without secondary activities or can easily be obtained directly in the form of an enzyme mixture as produced by the process for the recovery of enzymes from microorganisms; such enzyme mixtures as produced by the process for recovery from the microorganism normally include, in addition to a principal enzyme, various subsidiary enzymes (so-called secondary activities), which as a rule develop a favorable synergistic secondary effect. Thus, in general terms, the enzyme or enzyme mixture can be a hydrolase, preferably from the group comprising carbohydrases, proteases, lipases and esterases, or an oxynitrilase, tannase, chitinase, keratinase or oxidase, or a mixture of these enzymes. The carbohydrases for the process according to the invention are selected e.g. from beta-glucanases, cellulases, amylases, pentosanases (e.g. endopentosanases), pectinases and xylanases. Within the framework of the invention, it is also possible to use other feed enzymes, e.g. arabanases, hemicellulases, galactomannanases, polygalacturonases, phytases, glucoamylases, β-galactosidases, pullulanases, DRISELASE®, an enzyme mixture comprising cellulase, laminarinase, xylanase, pectinase, dextranase, amylase, protease, and other enzymes like lysozyme or muramidases. If oxidases are used, they can be glucose oxidases or peroxidases. The proportion (amount) of enzyme introduced depends here on the individual specific enzymatic activity and the desired activity in the finished enzyme pregranules. For example, pentosanase normally has a high specific activity and can assure an adequate enzymatic activity in the finished enzyme pregranules in amounts of only 0.01 to 0.1 part by weight. The enzyme or enzyme mixtures are prepared using bacteria in general, and those of the genus Pseudomonas or Bacillus in particular, or fungi in general, and those of the genus Aspergillus, Trichoderma, Rhizopus, Penicillium or Irpex in particular. If desired, the structural genes of the enzymes can also be cloned into suitable strains of microorganisms and expressed. Any microorganism which takes up the enzyme DNA to be cloned, via a plasmid (episome) or a genome (chromosome), and can perform the corresponding functions, is suitable per se for this purpose.

The enzyme or enzyme mixture used in the process according to the invention can be employed in the form of a powder or an aqueous solution of the enzyme or enzyme mixture, advantageous enzymes or enzyme mixtures being enzyme preparations such as those conventionally obtained by industrial production. Such enzyme preparations normally contain not only a single enzyme or a mixture of enzymes, but also minor amounts of other subsidiary substances produced by the preparative process. Examples of such subsidiary substances are salts which are added for precipitation of the enzyme from the mother liquor, such as that obtained after separation of the biomass from a fermentation broth, and which can be partially included by the enzyme precipitate during precipitation. The enzymes or enzyme mixtures can also contain conventional enzyme stabilizers and conventional adjusters and preservatives as other subsidiary substances. Examples of such subsidiary substances are alcohols, glycols and glycol ethers, such as 1-methoxy-2-propanol, isopropanol and butyl diglycol, sodium benzoate, calcium salts, glucose, parabens, potassium and sodium sorbate and sodium chloride. If aqueous solutions of the enzyme or enzyme mixture are used, these can be prepared by the subsequent dissolution of powdered enzymes or enzyme mixtures; alternatively, in another variant, the mother liquors, such as those obtained after separation of the biomass from the fermentation solution, can also be used directly, if appropriate after concentration or dilution. Such aqueous solutions of enzymes or enzyme mixtures normally still contain a small proportion of subsidiary substances produced by the preparative process, in addition to the actual enzymatic activity or, in the case of enzyme mixtures, in addition to the various enzymatic activities. On the one hand, enzyme mixtures can be obtained directly by fermentation, in which case the enzymes conventionally formed by the microorganism used are present as a mixture with one another in natural proportions. On the other hand, however, enzyme mixtures can also be prepared by simply mixing commercially available individual enzymes.

Granulation aids which can be used in the process according to the invention are enzyme-compatible binders, fillers and/or organic solvents which are safe in terms of nutritional physiology. Advantageous binders are especially degraded soluble starch and/or wheat gluten.

In one particular embodiment of the process according to the invention, the constituents of the enzyme pregranules, premixed in pulverulent form ("premix"), are fed batchwise or continuously into the high-speed mixer, into which water or an aqueous solution, if appropriate with granulation aids (e.g. binders) and/or enzyme or enzyme mixture dissolved therein, is metered, again batchwise or continuously, in an amount suitable for adjusting the moisture content, and the moist enzyme granules are then formed by intimate mixing and, after a given residence time, removed or continuously withdrawn from the high-speed mixer.

The invention further relates to the enzyme pregranules prepared by the process according to the invention, which are particularly suitable for incorporation into the particles of a granular animal feed. Another feature of such enzyme granules according to the invention is especially that they comprise 0.08 to 22% by weight (solids) of enzyme or enzyme mixture, 55 to 96.92% by weight (moisture-free solids) of a flour grade with an extraction rate of 30% to 100%, the flour grade having been obtained by grinding a flour base which may have been washed and/or purified beforehand and has been treated with dry superheated steam, if appropriate, up to a total of 18.5% by weight of granulation aids (calculated as anhydrous substance), and 3 to 12% by weight of moisture, the sum of the constituents comprising enzyme or enzyme mixture, flour solids, moisture and, if appropriate, granulation aid being 100% by weight.

Advantageous enzyme pregranules according to the invention comprise 0.08 to 11% by weight (solids) of enzyme or enzyme mixture, 66 to 96.92% by weight (moisture-free solids) of a flour grade with an extraction rate of 30% to 100%, the flour grade having been obtained by grinding a flour base treated with dry superheated steam, if appropriate, up to a total of 14.5% by weight of granulation aids (calculated as anhydrous substance), and 3 to 12% by weight of moisture, the sum of the constituents comprising enzyme or enzyme mixture, flour solids, moisture and, if appropriate, granulation aid being 100% by weight.

Particularly preferred enzyme pregranules according to the invention comprise 1.9 to 7.8% by weight (solids) of enzyme or enzyme mixture, 76 to 94.6% by weight (moisture-free solids) of a flour grade with an extraction rate of 30% to 100%, the flour grade having been obtained by grinding a flour base treated with dry superheated steam, a total of 0.5 to 5.4% by weight of granulation aids (calculated as anhydrous substance), and 3 to 12% by weight of moisture, the sum of the constituents comprising enzyme or enzyme mixture, flour solids, moisture and, if appropriate, granulation aid being 100% by weight.

The process according to the invention provides advantageous enzyme pregranules with stable activity for incorporation into the particles of a granular animal feed. The enzyme pregranules according to the invention, provided by said process, have various advantages in terms of further processing, i.e. in terms of incorporation into the particles of the granular animal feed. Firstly, the enzyme pregranules according to the invention are unusually stable to heat, pressure and friction. This enables the enzyme pregranules to be incorporated into the particles of a granular animal feed by conventional extrusion processes without substantial activity losses occurring during the conditioning step (jetting with superheated steam) and subsequent extrusion step (pressure and friction stress) for the production of pellets. The enzyme pregranules according to the invention therefore make the enzymes available in a form which enables them to withstand the high stress in the conditioning and extrusion steps of the process for the manufacture of granular animal feeds. The invention therefore further relates to the use of the enzyme pregranules prepared according to the invention for the manufacture of granular animal feeds and especially for the manufacture of such granular animal feeds where the enzyme is to be incorporated into the particles of the granular animal feed (i.e. so-called animal feed pellets) with maximum homogeneity and with protection against inactivation by extrusion processes.

As well as the good stability under stress during the manufacture of granular animal feeds (stability to heat, pressure and friction), the enzyme pregranules according to the invention have a number of other favorable properties. Thus the enzyme pregranules according to the invention exhibit an outstanding storage stability and, in particular, have an extremely low bacterial contamination which is negligible under any circumstances. They are free-flowing and therefore exhibit a good flowability and good metering properties. Furthermore, according to the test methods conventionally used in the feed industry, they show no tendency to cake. As regards the test methods conventionally used in the feed industry for dust determination, no tendency to form dust is observed either. The enzyme pregranules according to the invention are also within an advantageous particle size range, ensuring in particular that they can also be favorably mixed and incorporated into the formulation constituents of granulated animal feeds; the particles of enzyme pregranules according to the invention show no tendency to demix and can therefore be mixed well with the feed constituents in the extrusion process and incorporated (dispersed) well into the granular feed.

The following Examples will illustrate the above invention in greater detail without however limiting its scope.

EXAMPLE 1
Preparation of the Flour (Superheated Steam Treatment and Grinding)

The superheated steam treatment of the flour bases (whole grains or leguminous fruits) was carried out in a sterilizer of the following construction:

- a steam-heated warming screw, temperature 40 to 50° C.;
- a heat-insulated continuous steamer (vertical conical cylinder of height 5 m, top diameter 40 cm, bottom diameter 60 cm; temperature 100 to 110° C.);
- three annular steam nozzles in the upper region of the steamer and three vertical steam lances in the lower region;
- a steam-heated discharge screw;
- a downstream fluidized bed dryer and a fluidized bed cooler connected thereto.

The grains or legume particles were fed continuously into the conical steamer by means of the steam-heated warming screw. They were then treated with dry superheated steam (excess pressure reduced from 8 bar to 0.8 bar) via the three annular nozzles and three steam lances. The temperature of the material in the steamer was ca. 100° C. and the residence time ca. 40 minutes. The treated grains or legume particles were discharged via a steam-heated screw, through which the treated material was transferred to a fluidized bed dryer for the removal of steam and any condensate formed during the treatment. After cooling in a fluidized bed cooler connected thereto, the treated grains or legume particles were ground to the desired extraction rate in a manner conventional per se.

The flours obtained after superheated steam treatment had the following average properties:

- moisture content ca. 10 to 15% by weight (±2% by weight);
- total bacterial count below 100/g;
- 25 g samples were negative for *E. coli*, Salmonella and *Pseudomonas aeruginosa*; yeasts and molds were also undetectable.

The flours treated with superheated steam according to the invention were thus of outstanding microbiological purity. This high microbiological purity was also maintained for high extraction rates (high proportion of husks in the flour). The flours treated according to the invention were outstandingly suitable for the subsequent granulation of feed enzymes under mild conditions, especially under conditions without heat treatment or thermal bacterial count reduction.

EXAMPLE 2
Preparation of Enzyme Pregranules According to the Invention

To prepare enzyme pregranules according to the invention for incorporation into granular feed, enzyme preparations and cereal and/or legume flours obtained according to Example 1 were prepared by the agglomeration of a pulverulent starting mixture, with the addition of granulating liquid. The pulverulent starting mixture of enzyme preparation and cereal or legume flour was intimately mixed in a continuous high-speed mixer/agglomerator of the Flexomix type (from Schugi), with the granulating liquid being sprayed in, and the resulting granules were then dried in a continuous fluidized bed dryer. The undersize material (<100 µm) was blown out of the fluidized bed dryer (pneumatic classification) and the oversize material (>800 µm) was screened off and ground. The rejected particles were completely recycled into the granulation process.

The enzyme preparations used were a commercially available pentosanase preparation and a commercially available cellulase preparation. Both enzyme preparations are so-called powdered enzyme concentrates.

| Enzyme* | Pentosanase preparation/Activity** | Cellulase preparation/Activity** |
|---|---|---|
| Pentosanase | 1,030,000 EU/g (standard activity) | 160,000 EU/g |
| beta-Glucanase | 350 EU/g | 720 EU/g |
| alpha-Amylase | 8,800 EU/g | 107,000 EU/g |
| Galactomannanase | 4,300 EU/g | 13,300 EU/g |
| Cellulase | 16,000 EU/g | 30,900 EU/g (standard activity) |

*"natural" principal and subsidiary enzymes, i.e. those originating from the manufacturing process
**enzymatic activity units acccording to established standard methods of determination The flour used in this example was wholemeal wheat flour with an extraction rate of 100%. The specification of the particle size distribution of the wholemeal wheat flour used (measured with an Alpine A 200 LS laboratory pneumatic screen) was as follows (mean values):

| Particle size range | Proportion in % by weight (specification) |
|---|---|
| ≥300 µm | ca. 4 |
| <300 to ≥250 µm | ca. 10 |
| <250 to ≥200 µm | ca. 10 |
| <200 to ≥150 µm | ca. 15 |
| <150 to ≥100 µm | ca. 15 |
| <100 to ≥50 µm | ca. 20 |
| <50 µm | ca. 26 |

For the granulation, it is found to be advantageous if the proportion of fines (<50 µm) in the flour used is kept as small as possible (e.g. especially below 30% by weight).

The pulverulent starting mixture of enzyme preparation and flour used in the granulation process comprised 95 parts by weight of wholemeal wheat flour as substrate and 5 parts by weight of powdered enzyme concentrate. The pulverulent starting mixture was agglomerated with an aqueous spraying solution containing 4% by weight of dissolved modified starch. Examples of other process conditions are given in Table I and the product properties of the enzyme pregranules, obtained according to the invention, for incorporation into granular animal feeds are given in Table II.

Enzyme pregranules of outstanding microbiological quality, with correct specifications in respect of particle size distribution and activity and with very good technological granule properties, were prepared with minimal weight losses (<3% by weight).

TABLE I

Process conditions for the preparation of enzyme pregranules according to the invention

| | Pentosanase pregranules | | Cellulase pregranules | |
|---|---|---|---|---|
| | Mass flow rate, kg/h | Moisture content, % by weight | Mass flow rate, kg/h | Moisture content, % by weight |
| Weighing belt up-stream of Schugi mixer | 550 | 13.1 | 550 | 13.1 |
| 4% starch solution | 125 | 96.0 | 115 | 96.0 |
| Outlet of Schugi mixer | 675 | 29.1 | 665 | 26.3 |
| Recycled undersize material (fluidized bed dryer) | 118 | 11.6 | 92 | 10.6 |
| End product | 403 | 7.9 | 443 | 7.6 |
| Weight yield (corrected for moisture) | 98% by weight | | 97% by weight | |
| Product temperature in fluidized bed dryer | | | | |
| Segment 1 | | 50° C. | | 52° C. |
| Segment 2 | | 48° C. | | 50° C. |
| Segment 3 | | 53° C. | | 52° C. |
| Segment 4 | | 55° C. | | 56° C. |
| Speed of rotation of Flexomix | | 3378 rpm* | | 3484 rpm* |

*rpm = revolutions per minute

TABLE II

Product properties of enzyme pregranules according to the invention

| | Pentosanase pregranules | Cellulase pregranules |
|---|---|---|
| Activity | 3160 EPU/g[1)] | 1264 CU/g[2)] |
| Bulk density | 532 g/l | 500 g/l |
| Dust index | 0* | 0* |
| Flow factor | 28* | 56* |
| Caking test | 0* | 0* |
| Particle size distribution of end product | | |
| >800 μm (oversize material) | 0* | 0* |
| >500–800 μm | 26% | 21% |
| >250–500 μm | 52% | 57% |
| 100–250 μm | 21% | 22% |
| <100 μm (undersize material) | 0.2% | 0.1% |
| Bacterial counts of end product | | |
| Total bacterial count | 2000/g | 1700/g |
| Coliform bacteria | <30/g | <30/g |
| E. coli | neg. in 25 g | neg. in 25 g |
| Salmonellae | neg. in 25 g | neg. in 25 g |
| Pseudomonas aeruginosa | neg. in 25 g | neg. in 25 g |
| Yeasts | <200/g | <200/g |
| Molds | <200/g | <200/g |

*criteria in respect of technological granulation properties (measured by standard methods):
dust index 0–2: dust-free
flow factor > 10: free-flowing
caking test < 5: low caking tendency
[1)]EPU = activity which gives a relative fluidity change of 1 in one minute in a defined oat husk dextran
[2)]CU = activity which gives a relative fluidity change of 1 in 5 minutes in a carboxymethyl cellulose substrate

EXAMPLE 3

Incorporation of the enzyme pregranules into particles of a granular animal feed (animal feed pellets)

In a granulator ("pelletizer"), the enzyme pregranules prepared according to the invention in Example 2 were mixed into a feed premix in a manner similar to that used in practice, heat-conditioned and then granulated ("pelleted") by extrusion.

The typical apparatus used for pelleting the mixed feed comprised a premixer for mixing the solid components, a metering vessel, a short-term conditioner for adjusting the saturated steam to ca. 3% (product temperature 60 to 70° C.), a pelleting press (product temperature 65 to 80° C.) and a cooling screen.

The composition of the feed premixes into which the enzyme pregranules according to the invention (with pentosanase or cellulase) were incorporated is indicated in Table III. The experimental and analytical data from the pelleting tests with the given feed premix and pregranules according to the invention are shown in Table IV. With the indicated temperature profile having a maximum of 73° C. in the case of pentosanase pregranules and 81° C. in the case of cellulase pregranules, very high residual activities are found after pelleting, being 91% or 94% of the enzymatic activity introduced; such high enzymatic activities are not obtained when using enzymes according to the state of the art (cf. results of comparative tests on enzyme preparations according to the state of the art in Table IV).

TABLE III

Feed premixes for granulation or pelleting tests with enzyme pregranules according to the invention

| | for granular feed with | |
|---|---|---|
| | pentosanase | cellulase |
| Feed component | | |
| Wheat | 37.1% by weight | 24.8% by weight |
| Barley | — | 33.6% by weight |
| Maize | 18.9% by weight | — |
| Coarse soya meal 44% | 14.5% by weight | 13.4% by weight |
| Peas | 12.6% by weight | 13.2% by weight |
| Animal 55 | 8.4% by weight | 9.1% by weight |
| Animal fat | 3.2% by weight | — |
| Field beans | 3.1% by weight | 3.5% by weight |
| Bonemeal | 2.2% by weight | 2.4% by weight |
| Ingredient | | |
| Moisture | 11.4% by weight | 11.8% by weight |
| Raw fat | 5.5% by weight | 2.9% by weight |
| Raw fiber | 3.7% by weight | 5.8% by weight |
| Raw protein | 19.8% by weight | 21.2% by weight |
| Raw starch | 41.4% by weight | 37.8% by weight |
| Raw ash | 6.6% by weight | 6.0% by weight |
| Physical property | | |
| Density | 1.34 g/cm$^3$ | 1.38 g/cm$^3$ |
| Bulk density | 0.69 g/cm$^3$ | 0.64 g/cm$^3$ |
| Tap density | 0.74 g/cm$^3$ | 0.60 g/cm$^3$ |
| Angle of repose | 39.0° | 42.0° |
| Particle size $x_{50}$ | 0.71 mm | 0.58 mm |

TABLE IV

Experimental and analytical data from the pelleting tests with pentosanase and cellulase (in each case as enzyme pregranules according to the invention) and enzymes of the state of the art

|  | T °C. | Moisture content % by weight | Activity EPU/kg* | Relative activity % | T °C. | Moisture content % by weight | Activity EPU/kg* | Relative activity % |
|---|---|---|---|---|---|---|---|---|
|  |  |  | Granular feed with |  |  |  |  |  |
| according to the invention |  | pentosanase |  |  |  | cellulase |  |  |
| before short-term conditioner | 17 | 11.4 | 1790 | 100 | 20 | 12.3 | 476 | 100 |
| after short-term conditioner | 65 | 14.4 | 1678 | 93.7 | 70 | 15.4 | 510 | 107 |
| after press | 73 | 14.8 | — | — | 81 | 15.2 | — | — |
| after cooler | 17 | 12.5 | 1621 | 90.6 | 21 | 12.7 | 448 | 94 |
|  |  |  | Granular feed with |  |  |  |  |  |
| comparative tests |  | pentosanase (according to the state of the art) |  |  |  | cellulase (according to the state of the art) |  |  |
| before short-term conditioner | 17 | 11.4 | 2242 | 100 | 20 | 12.3 | 495 | 100 |
| after short-term conditioner | 65 | 14.4 | 1561 | 69 | 71 | 15.4 | 475 | 96 |
| after press | 73 | 14.8 | — | — | 81 | 15.2 | — | — |
| after cooler | 17 | 12.5 | 1685 | 77 | 20 | 12.7 | 285 | 58 |

*EPU = activity which gives a relative fluidity change of 1 in one minute in a defined oat husk dextran

EXAMPLE 5

Heat stability of enzyme pregranules according to the invention in an animal feed matrix (model experiment)

To demonstrate the high heat stability of the enzyme pregranules prepared according to the invention, the heat stability of enzyme pregranules according to the invention in a matrix of different animal feeds was tested in a model system. This was done by mixing cellulase or pentosanase pregranules according to the invention with poultry feed (conventional constituents). The enzyme was incorporated into the feed mix in an amount of 5% by weight.

The measurements were made as follows:

Small glass tubes (10×1 cm) were filled with 5 g of the feed mix and then kept in a thermostatted water bath for a particular time at a particular temperature. After the temperature treatment, the tube was immediately cooled in an ice-water bath. The residual cellulase activity was determined by a calorimetric method using a reference activity standard. This test was based on the enzymatic hydrolysis of the internal beta-1,4 glucosidic linkages in a defined azurin-crosslinked cellulose. The activity recovered in % of the activity originally introduced is shown in Table V for the tested enzymes pentosanase (Table Va) and cellulase (Table Vb). It is seen that cellulase, with recovered activities of over 95% after treatment for more than one hour at temperatures below 80° C., is very stable in the feed mix. Pentosanase is also seen to be very temperature-stable in the feed mix with a residual activity of 83% at temperatures of 83° C. for a test period of 60 minutes. For very short periods, e.g. 5 minutes, even higher residual activities are recovered (e.g. almost 100% at 95° C., 5 minutes)

Comparable enzyme formulations of the state of the art prove to be appreciably more sensitive to temperature in the feed compositions.

TABLE Va

Temperature stability of enzyme pregranules according to the invention in the feed matrix: pentosanase as enzyme

| Test no. | Time [min] | Temperature [° C.] | Residual activity [%] |
|---|---|---|---|
| 1.1 | 0 | 70 | 100 |
| 1.2 | 5 | 70 | 130 |
| 1.3 | 33 | 70 | 94 |
| 1.4 | 33 | 70 | 72 |
| 1.5 | 60 | 70 | 81 |
| 1.6 | 60 | 70 | 72 |
| 2.1 | 0 | 78 | 100 |
| 2.2 | 23 | 78 | 102 |
| 2.3 | 42 | 78 | 91 |
| 3.1 | 0 | 83 | 100 |
| 3.2 | 5 | 83 | 119 |
| 3.3 | 5 | 83 | 130 |
| 3.4 | 60 | 83 | 83 |
| 3.5 | 60 | 83 | 89 |
| 4.1 | 0 | 87 | 100 |
| 4.2 | 23 | 87 | 96 |
| 4.3 | 42 | 87 | 89 |
| 5.1 | 0 | 95 | 100 |
| 5.2 | 5 | 95 | 111 |
| 5.3 | 5 | 95 | 120 |
| 5.4 | 23 | 95 | 75 |
| 5.5 | 33 | 95 | 60 |
| 5.6 | 60 | 95 | 47 |

TABLE Vb

Temperature stability of enzyme pregranules according to the invention in the feed matrix: cellulase as enzyme

| Test no. | Time [min] | Temperature [° C.] | Residual activity [%] |
|---|---|---|---|
| 1.1 | 0 | 70 | 100 |
| 1.2 | 5 | 70 | 110 |
| 1.3 | 33 | 70 | 98 |
| 1.4 | 33 | 70 | 98 |
| 1.5 | 60 | 70 | 94 |
| 1.6 | 60 | 70 | 103 |
| 2.1 | 0 | 78 | 100 |
| 2.2 | 23 | 78 | 97 |
| 2.3 | 42 | 78 | 93 |
| 3.1 | 0 | 83 | 100 |
| 3.2 | 5 | 83 | 102 |
| 3.3 | 5 | 83 | 105 |
| 3.4 | 60 | 83 | 91 |
| 3.5 | 60 | 83 | 86 |
| 4.1 | 0 | 87 | 100 |
| 4.2 | 23 | 87 | 88 |
| 4.3 | 42 | 87 | 87 |
| 5.1 | 0 | 95.5 | 100 |
| 5.2 | 5 | 95.5 | 96 |
| 5.3 | 5 | 95.5 | 99 |
| 5.4 | 23 | 95.5 | 91 |
| 5.5 | 33 | 95.5 | 71 |
| 5.6 | 60 | 95.5 | 65 |

Where reference is made to enzymatic activities in the present patent application, the activity of the enzyme in question was determined by standard methods which are conventional per se and familiar to those skilled in the art.

What is claimed is:

1. A process for the preparation of enzyme pregranules with stable enzymatic activity comprising:

providing a flour base;

treating the flour base with dry superheated steam;

grinding the flour base to obtain an organic flour grade;

providing an enzyme or enzyme mixture;

combining 0.01 to 20 parts by weight of the enzyme or enzyme mixture, calculated as the dry solids content thereof, with 80 to 99.99 parts by weight, including moisture, of the organic flour grade with an extraction rate of 30% to 100%, the total parts by weight of the enzyme or enzyme mixture and the organic flour grade equaling 100 parts by weight;

combining up to 20 parts by weight of a granulation aid, calculated as anhydrous granulation aid with the enzyme or enzyme mixture and the organic flour grade, and sufficient water to adjust the moisture content of the moist granules to 20 to 50% by weight, based on the total weight of the moist granules, to form adhesive-free moist granules; and drying the moist granules to form enzyme pregranules, wherein the process does not include a pelletizing step.

2. A process as claimed in claim 1, wherein the enzyme or enzyme mixture is 0.01 to 10 parts by weight, the flour grade is 90 to 99.99 parts by weight, the granulation aid is up to a total of 15 parts by weight, and the amount of water is sufficient to adjust the moisture content to 25 to 40% by weight.

3. A process as claimed in claim 2, wherein the moisture content is adjusted to 25 to 35% by weight.

4. A process as claimed in claim 2, wherein the amount of granulation aid is 0.5 to 5 parts by weight.

5. A process as claimed in claim 2, wherein the amount of flour grade is 93 to 98 parts by weight.

6. A process as claimed in claim 2, wherein the amount of enzyme or enzyme mixture is 2 to 7 parts by weight.

7. A process as claimed in claim 1, wherein the extraction rate of the flour grade is 50% to 100%.

8. A process as claimed in claim 7, wherein the extraction rate of the flour grade is 70% to 100%.

9. A process as claimed in claim 1, wherein grain, leguminous fruits and/or fruits of the Malavaceas family are used as the flour base for obtaining the flour grade.

10. A process as claimed in claim 1, wherein the flour base has been treated with dry superheated steam at a temperature of about 100 to about 110° C., under approximately normal pressure to a slight excess pressure, for a treatment time of up to about 1 hour.

11. A process as claimed in claim 1, wherein moist granules with a particle size range of 100 to 800 μm, are produced.

12. A process as claimed in claim 11, wherein the moist granules have a particle size range of 100 to 500 μm.

13. A process as claimed in claim 1, wherein the enzyme or enzyme mixture is used in the form of a powder or an aqueous solution of the enzyme or enzyme mixture.

14. A process as claimed in claim 1, wherein the enzyme or enzyme mixture is hydrolase, selected from the group consisting of a hydrolase, an oxynitrilase, a tannase, a chitinase, a keratinase, an oxidase, and a mixture thereof.

15. A process as claimed in claim 14, wherein an enzyme with secondary activities or an enzyme mixture is used.

16. A process as claimed in claim 14, wherein the oxidase is a glucose oxidase or peroxidase.

17. A process as claimed in claim 8, wherein the enzyme is lysozyme or muramidase.

18. A process as claimed in claim 14, wherein the enzyme or enzyme mixture is a hydrolase selected from the group consisting of a carbohydrase, a protease, a lipase, and an esterase.

19. A process as claimed in claim 1, wherein the granulation aid is an enzyme-compatible binder, a filler or an organic solvent of natural origin which is safe in terms of nutritional physiology.

20. A process as claimed in claim 19, wherein the binder is degraded soluble starch and/or wheat gluten.

21. A process as claimed in claim 1, wherein the constituents for the enzyme pregranules, premixed in pulverulent form, are fed batchwise or continuously into the high-speed mixer, into which water or an aqueous solution with a granulation aid or enzyme or enzyme mixture dissolved therein, is metered in, batchwise or continuously, in an amount suitable for adjusting the moisture content, and, after a given residence time, the moist enzyme granules are removed or continuously withdrawn from the high-speed mixer.

22. A process as claimed in claim 1, wherein the dried granules are freed of undersize and/or oversize material by screening.

23. Enzyme pregranules with stable activity for incorporation into particles of a granular animal feed, wherein the enzyme pregranules are obtained by a process as claimed in claim 1.

24. Enzyme granules as claimed in claim 23 which comprise 0.08 to 22% by weight of enzyme or enzyme mixture, 55 to 96.92% by weight of a flour grade with an extraction rate of 30% to 100%, the flour grade having been obtained by grinding a flour base treated with dry superheated steam, up to a total of 18.5% by weight of granulation aid, calculated as anhydrous substance, and 3 to 12% by weight of moisture, the sum of the constituents being 100% by weight.

25. A process for the manufacture of a granular animal feed which comprises mixing enzyme pregranules as claimed in claim 16 into conventional animal feed constituents and processing this mix to a homogeneous granular animal feed by extrusion.

* * * * *

UNITED STATES PATENT AND TRADEMARK OFFICE
CERTIFICATE OF CORRECTION

PATENT NO. : 6,221,406 B1
DATED : April 24, 2001
INVENTOR(S) : Meschonat et al.

It is certified that error appears in the above-identified patent and that said Letters Patent is hereby corrected as shown below:

Title page,
Item [76], the addresses of the inventors are:
-- Beate Meschonat, Wendehagen 19, 30419 Hanover, Germany
Hubert A. Herrmann, Wanneweg 25, 38162 Cremlingen-Weddel, Germany
Rolf Spannagel, Zum Hahnenkamp 20, 32629 Husum/Ngb., Germany
Vera Sander, Mühlenweg 11, 30826 Garbsen, Germany
Gerhard Konieczny-Janda, Schöneberger Straße 23, 30982 Pattensen, Germany
Mario Sommer, Am Pfaffenroth 14, 61389 Schmitten, Germany Column 16,
Line 15, correct claim 9, in the second line, by replacing "Malavaceas" with
-- Malvaceae --.

Signed and Sealed this

Twenty-third Day of July, 2002

*Attest:*

JAMES E. ROGAN
*Attesting Officer*   *Director of the United States Patent and Trademark Office*